United States Patent
Godfrey et al.

(10) Patent No.: US 7,963,151 B2
(45) Date of Patent: Jun. 21, 2011

(54) CARTRIDGE FOR A FLUID SAMPLE ANALYSER

(75) Inventors: Daniel Peterson Godfrey, Cambridge (GB); Mark John Frogley, Huntington (GB)

(73) Assignee: Akubio Limited (GB)

( * ) Notice: Subject to any disclaimer, the term of this patent is extended or adjusted under 35 U.S.C. 154(b) by 591 days.

(21) Appl. No.: 11/817,851

(22) PCT Filed: Mar. 31, 2006

(86) PCT No.: PCT/GB2006/001162
§ 371 (c)(1),
(2), (4) Date: Sep. 3, 2008

(87) PCT Pub. No.: WO2006/103439
PCT Pub. Date: Oct. 5, 2006

(65) Prior Publication Data
US 2009/0100914 A1    Apr. 23, 2009

(30) Foreign Application Priority Data
Apr. 1, 2005   (GB) ................... 0506710.3

(51) Int. Cl.
*G01N 1/00*   (2006.01)
(52) U.S. Cl. ......................... 73/64.56; 73/863

(58) Field of Classification Search ............. 73/64.56, 73/863, 864.81, 864.91
See application file for complete search history.

(56) References Cited

U.S. PATENT DOCUMENTS

| 6,196,059 B1 | 3/2001 | Kösslinger |
| 6,990,852 B2 | 1/2006 | Berndt |
| 7,093,482 B2 | 8/2006 | Berndt |
| 2004/0189311 A1 | 9/2004 | Glezer |

FOREIGN PATENT DOCUMENTS

| WO | WO-02/12873 A2 | 2/2002 |
| WO | WO-2005/121769 A1 | 12/2005 |
| WO | WO-2006/010206 A1 | 2/2006 |

*Primary Examiner* — Hezron Williams
*Assistant Examiner* — Rodney T Frank
(74) *Attorney, Agent, or Firm* — Barnes & Thornburg LLP (57) ABSTRACT

A cartridge for apparatus for analysing a sample comprising a fluid as a flow cell for receiving the sample. The cell is formed from a substantially rigid support surface (102), a sensor comprising an electrical mechanical transducer (92), for example a wafer of quartz crystal and adhesive means, such as double sided adhesive tape (100) attaching the sensor to the support surface. The support surface and sensor are spaced from each other by a membrane, which may form part of the double sides adhesive tape so as to define the flow cell between the support surface and the sensor. The flow cell also has an opening (for example, 111) through which, in use, the sample passes. The sensor, forming part of the flow cell, comes into contact with the sample to enable the sample to be analysed.

29 Claims, 5 Drawing Sheets

CARTRIDGE FOR A FLUID SAMPLE ANALYSER

STATEMENT REGARDING FEDERALLY SPONSORED RESEARCH OR DEVELOPMENT

This invention is made with US Government support under Grant No: 5U01A1061243-05 awarded by USAMRIID and NIAID. The Government has certain rights in the invention.

This invention relates to a cartridge for apparatus for analysing a sample comprising a fluid, and in particular to a cartridge having a sensor, for performing that analysis, comprising an electrical-mechanical transducer.

BACKGROUND TO THE INVENTION

The invention is applicable to apparatus in which a transducer modifies an applied electrical signal, in particular piezoelectric transducers, for example a quartz crystal microbalance system, where the transducer vibrates at a frequency at or close to its resonant frequency.

The transducer typically has an active surface on which a receptor group is immobilised. That group has a chemical affinity or reactivity towards the substance to be detected or analysed. The substance to be analysed is normally present in a fluid which is brought into contact with the active surface of crystal.

Physical, chemical and biochemical interactions between the receptor group on the surface and the substance cause a change in the mass attached to the surface (and in other physical properties of the active surface), and these affect the vibrational characteristics, in particular the resonant frequency, of the crystal. Analysis of these effects can be used to obtain qualitative and/or quantitative data on the substance.

In some types of known apparatus, the quartz crystal sensor is formed as part of flow cell which is connected to a sample delivery/removal system for passing a sample to be analysed through the cells so that the sample comes into contact with the crystal. The apparatus will include drive measurement circuitry connected to the crystal and operable to vibrate the crystal and to detect and/or measure the changes in the crystal's vibrational characteristics.

Replacement of the transducer is frequently necessary, particularly in the field of bio-sensors, if a number of different substances in fluid sample are to be analysed or if the receptor coating on the crystal cannot be used more than once.

In that connection it is known to provide the crystal and the flow cell in a single cartridge which may be readily inserted into and removed from apparatus providing the electrical circuitry and the sample delivery/removal system. An easily manufactured flow cell which is disposable, yet easily and robustly mountable into the measurement apparatus is therefore highly desirable.

U.S. Pat. No. 6,196,059 shows a cartridge formed from an injection moulded component having an annular rib to which the crystal is adhered. The rib spaces the crystal from an opposed face to define a flow cell, and the injection moulded component also includes recesses for contacts at a position spaced from the crystal. The contacts are connected to crystal by electrical wires, and provide a means of connection between the crystal and the appropriate drive/measurement circuitry.

Such a cartridge is of a relatively complex construction and is therefore relatively expensive, especially since the cartridge is to be used as a disposable unit. In addition, the minimum distance between the crystal and the underlying surface, and hence the volume of the flow cell, is limited by the rib, which provides a lower limit on the height of the flow cell. This can prevent the flow cell from achieving rapid immobilisation times, and this correspondingly limits the speed of response of the apparatus. Additionally the cartridge requires a manual electrical connection operation between the terminal of the transducer and the instrument, which is inconvenient in operation.

In the analysis of biomechanical interactions available volumes of analyte fluid are frequently limited so the volume of the flow cell should be small. It is also known that measurements of kinetic properties of analyte receptor interactions can be limited by the diffusion of analyte to the surface of the transducer. In order to minimise this transport limitation, and preferably overcome it, the dimension of the flow cell in the direction perpendicular to the transducer surface should be minimised.

The mounting of electromechanical piezo-electrical transducers such as quartz crystal oscillators in such a way that the mounted transducer is free of residual stress, and forms a reliable fluid tight seal is an important design objective of such cells. WO2128372 and WO0247246 propose various means intended to achieve stress free mounting, but in these cases there results a relatively complex multipart design for fabricating a leak tight structure, and further, as with U.S. Pat. No. 6,196,059 above this results in a situation where it is difficult to obtain a low volume of the flow cell.

SUMMARY OF THE INVENTION

According to the invention, there is provided a cartridge for apparatus for analysing a sample comprising a fluid, the cartridge comprising a flow cell formed from a substantially rigid supporting surface, a sensor comprising electrical-mechanical transducer for performing said analysis; an adhesive means attaching the sensor to the support surface, and a membrane spacing the sensor from the support to define the flow cell between the support and the sensor, the flow cell also having an opening through which, in use, the sample passes.

The use of a combination of a membrane and an adhesive between the sensor and support surface enables the flow cell to be formed from relatively simple components, and hence to be relatively cheap. In particular, the support surface can take the form of a simple plate, rather than a support component formed by a dedicated injection moulding process.

Furthermore, since a membrane is used to space the sensor from the support surface, the flow cell can be very thin, so that the sensor can have a relatively rapid response.

Preferably, the membrane bounds the flow cell, the opening being provided in the support surface. The opening may be one of two such openings constituting inlet and outlet ports for the flow cell.

The adhesive may comprise an adhesive layer applied to or formed with the support surface, and a further adhesive layer applied to the sensor so that, in the course of assembly of the cartridge, the adhesive layers on the support surface and the sensor are bought into contact with opposite sides of the membrane to attach the sensor and support surface to the membrane, and hence to each other.

Preferably, however the membrane and adhesive means comprise a double sided adhesive membrane, preferably a single membrane comprising a substrate layer sandwiched between two adhesive layers.

The membrane may conveniently comprise a double sided adhesive tape.

The tape can be cut to a suitable width and punched with the shape of the flow cell(s) by conventional industrial processes.

The use of the tape to define the height of the flow cell gives rise to flexibility in the design of cartridge: a cartridge having a different height flow cell can be designed simply by choosing a different thickness of tape. The height of the flow cell can be quickly and cheaply changed by using different thicknesses of tape, rather than by redesign of mold for the other components of the cartridge. Thinner tapes provide flow cells having improved transport characteristics but in some instances thicker tapes may be preferable.

Preferably, the tape is flexible.

Preferably the membrane is non-compliant to ensure a uniform thickness of the flow cell and a rigid surface to support the transducer when electrical connections to the transducer are applied. Membranes which comprises a polyester carrier are suitable and preferred. The adhesive layers preferably comprise a cross-linking material which cures to form a non-compliant layer. Pressure sensitive adhesives are preferred.

The tape may be provided with an inert liner on one or both sides to enable the simple and consistent mechanical application of the membrane to the transducer or the plate.

Such tape is relatively cheap, and widely available, in a variety of thicknesses of carrier and adhesive.

Preferably, the support surface comprises a plate, which may to advantage have a fluid connector, constituting the opening, for engaging a complementary connector of a sample delivery system to enable a sample to be supplied to the flow cell.

Preferably, the connector is so sized and shaped as to make mating engagement with such a complementary connector. In this case, the connector is preferably a female connector, preferably comprising a passage for receiving a male connector constituted by a ferrule.

The female connector can be recessed into the cartridge so as not to protrude from the latter. This can contribute to the relatively compact construction of the cartridge and reduces the risk of damage to the connector before the cartridge is used.

Preferably, the connector is one of two such connectors, one for connection to the sample delivery system, the other for connecting an outlet of the flow cell to a sample removal system.

Preferably, the electrical-mechanical transducer comprises a plate, and may for example be a piezoelectric, piezo magnetic or acoustic sensor. More specifically, the sensor may be a quartz crystal microbalance.

Preferably, the sensor includes two electrodes for the connection to circuits for operating the sensor.

At least one of these electrodes may advantageously be in registry with the flow cell. In this case, one of the electrodes may be provided on the flow cell side of the side of the connector, the other on the opposite side. Preferably, the electrode on the flow cell side is the earth electrode, the other electrode being the driven electrode.

Preferably, the sensor includes thereon contacts for connecting two electrical connectors for connecting the sensor to circuitry for operating the latter. This avoids the need for separate contacts and connecting wires to be provided on the cartridge.

The apparatus may to advantage include a cover member attached to the support surface, the sensor being interposed between the support sensor and cover member.

Thus the cover member can provide protection for the sensor prior to use, which gives rise to a more robust construction of cartridge which may be more easily handled than a cartridge having an exposed sensor.

Preferably, the cover member is so spaced from the sensor as to make no contact with the latter.

Such a cover member will exert substantially no stresses or affect the tension in the sensor, and will therefore not adversely effect the accuracy of the sensor.

The cover member preferably includes one opening in registry with each sensor for an electrical connector for making contact with the electrode on the non flow cell side of the sensor to contact the sensor to the circuitry for operating the sensor.

Preferably, the support surface comprises a further plate. At least one of said plates may advantageously be provided with a bore (preferably a though bore) for laterally locating the cartridge.

Preferably, the cell is tapered at opposite end regions, the inlet and outlet of the flow cell each being located in a respective one of these regions.

Preferably, the flow cell is one of two such cells in the cartridge. Indeed it is within the scope of the invention for the cartridge to have more flow cells (for example four flow cells) and to be provided in conjoined arrays of multiple cartridges for example (1×4) or (4×4) arrays or a combination of these arrangements.

A cartridge in accordance with the invention can provide a low cost, easily manufactured, flow cell of a low volume suitable for minimising transport limitations in the diffusion of analytes to the transducer surface, and which comprises a transducer, the flow cell capable of being mounted and connected simply, robustly and reliably to a measurement instrument.

BRIEF DESCRIPTION OF THE DRAWINGS

The invention will now be described, by way of example only, with reference to the accompanying drawings, in which.

DETAILED DESCRIPTION

The cartridge shown in the drawings is for use as part of a quartz crystal microbalance apparatus, which includes a docking station for connecting each of two flow cells in the cartridge to a fluid delivery/removal system and for connecting a transducer in the form of a quartz crystal plate 92 to electrical circuitry for vibrating the crystal and measuring the crystal's vibrational characteristics. Such apparatus is described in the present applicant's co-pending UK patent application number 0506711.1

As is indicated above, the quartz crystal plate 92 forms part of the cartridge shown in the drawings. The plate is coated on one surface with gold in a pattern that defines a pair of drive electrodes 96 and 98, each of which is in registry with a respective one of two separate flow cells. The underside of the plate is also coated with gold to form a common earth electrode. A conductive track (not shown) runs from this electrode around the edge of the plate to the top surface of the plate to provide a contact for enabling a coda pin engaging the top surface of the plate to connect to the earth electrode.

The transducer 92 is adhered to the top surface of an adhesive membrane 100 the underside of which is adhered to a plate 102 the upper surface of which constitutes a support surface for the transducer 92.

The membrane 100 is a three layered structure of a total thickness of 85 microns, and comprising a polyester film carrier layer of 12 microns thickness sandwiched between two adhesive layers, each of a thickness of approximately 36.5 microns. It is possible that shrinkage of the adhesive layers occurs on curing. An example of suitable material for the membrane is the double sided adhesive tape sold under the trademark FASTOUCH. The membrane 100 has two generally diamond shaped apertures 104 and 106.

Each of the apertures 104 and 106 is in registry with a respective electrode 98 and 96, and thus with an active area of the quartz crystal. The membrane 100 spaces the transducer 92 from the upper surface of the plate 102 so that there is a small gap between each of two said active areas of the quartz crystal and the upper surface of the plate 102, each gap being bounded by the edge of a respective one of the two apertures 104 and 106. Each gap constitutes a respective flow cell which communicates with a respective pair of inlet/outlet passages 109-112 in the plate 102. Each passage leads into a female connector, such as the connectors 114 and 116 which is generally cylindrical and has a tapered end portion, each of the connectors being arranged to receive a respective ferrule of the fluid delivery/removal system of the apparatus.

Figure 1:
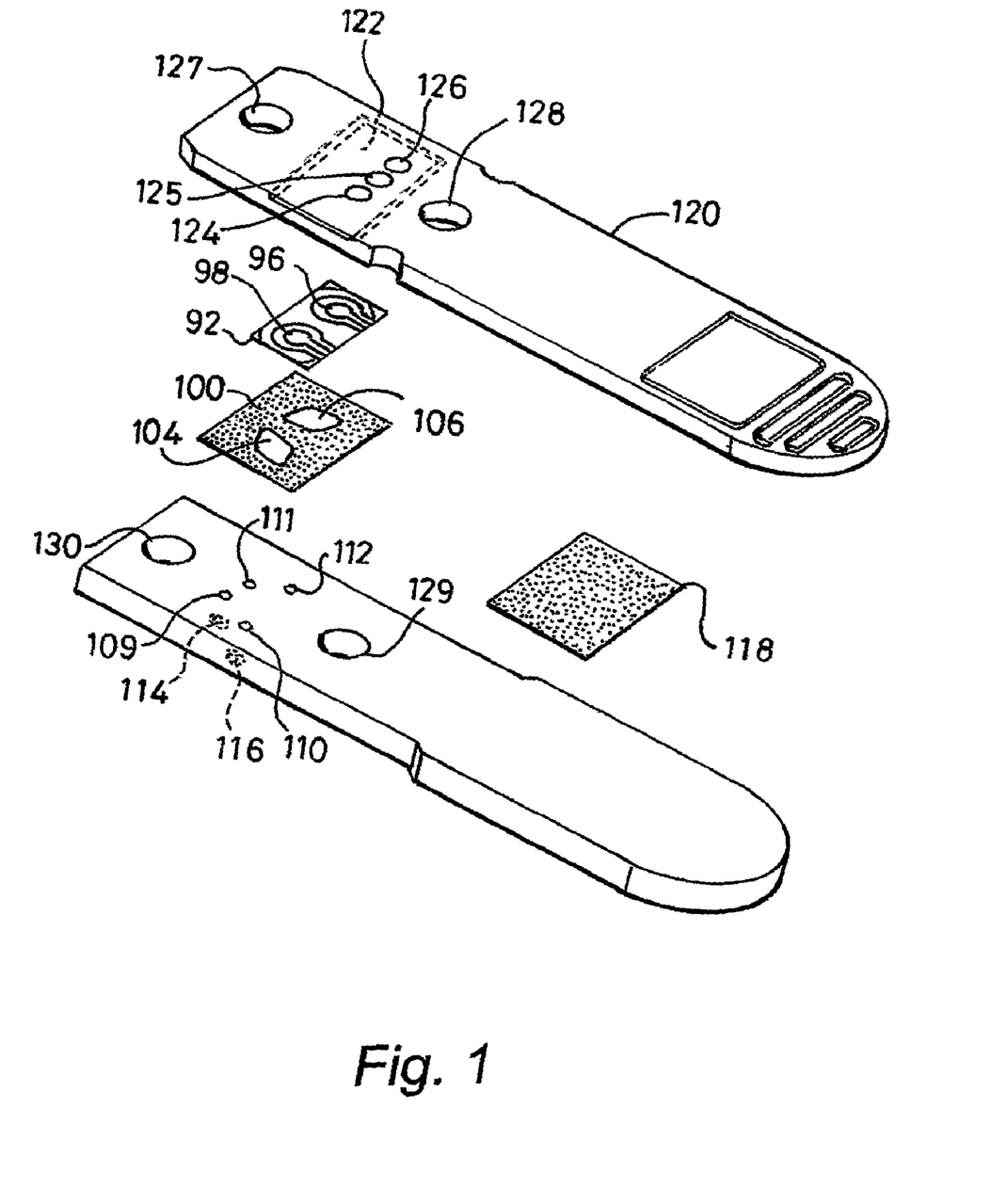
FIG. 1 is an exploded perspective view of a cartridge in accordance with the invention.

As can be seen from FIG. 1, the inlet and outlet for each flow cell are located at opposite end regions of the latter. Consequently, a sample introduced into the inlet of the flow cell will flow along the length of the flow cell to the outlet, during which period the sample will interact with the active surface of the crystal and the effect of that interaction will be measured.

As can be seen from FIG. 1, the flow cells are situated towards one end of plate 2, towards the other end of which there is provided a patch 118 of the same material as the membrane 100. The purpose of this patch is to help to adhere a top plate 120 to the bottom plate 102. The top plate 120 includes a recess 122 which, in the assembled cartridge, accommodates the sensor 92 so that the latter makes no contact with the plate 120. The membrane 100, however, does extend beyond the boundaries of the recess 122 so as to adhere the two plates 102 and 120 together at their forward ends.

As well as securing the transducer 92 in position and defining each flow cell, the membrane 100 provides a suitable seal, by virtue of the adhesive layers, for preventing fluid escaping from the flow cells.

The upper plate 120 includes through bores 124, 125 and 126 through which, in use, corresponding coda pins of the docking mechanism extend to make respective contact with the electrodes 96 and 98 and the earth contact of the transducer 92. Notches H in the upper plate serve to provide an initial location of the cartridge in the docking mechanism.

The two plates 102 and 120 also include large diameter through bores 127-130, the bore 127 in the plate 120 being in line with the bore 120 in plate 102, the bore 128 with the bore 129 so that there are two large bore through passages in the cartridge housing (defined by the plates 102 and 120). These passages, in use, accept lateral location pins (not shown) of the docking mechanism for assisting in the correct location of the cartridge. These pins also form a Faraday cage surrounding the transducer and connection pins.

After a cartridge has been inserted into the docking mechanism, the ferrules on the fluidic manifold are pressed into the female fluid connectors 114, 116 in the bottom plate of the cartridge with sufficient force to cause the ferrules to deform and thereby create a fluid seal.

Then each of the coda pins extend is extended into a respective aperture 124, 125 and 126 of the cartridge upper plate 120 to engage the drive electrode or, as the case may be the earth contact on the transducer.

The plates 102 and 120 are of an engineering plastics material which is inert to biological materials. Acrylic polymers such as Polymethyl methacrylate (PMMA) amongst many known in the art are suitable.

Optionally the polymer may be coated with a material which resists fouling by biological material.

The embodiment of sensor (shown in FIGS. 1-3) has a dual channel sensing plate 92 of quartz which carries an active gold layer on either side. The biochemically active side of the sensor coated with a continuous coating of gold and is connected to earth. the electrically driven side has a pattern in which the active areas (96 and 98) are circular, with contiguous rectangular areas 99 and 101 extending to the edge of the quartz plate. These rectangular areas provide four electrical contacts between the active electrodes and the Coda pins in the docking mechanism. The electrically active side (i.e. the side carrying the circular electrodes) is also provided with a "guard" earth electrode 97 which forms a respective ring around each driven circular area and serves to dampen any electrical cross-talk between the two or more resonators.

Figure 2:
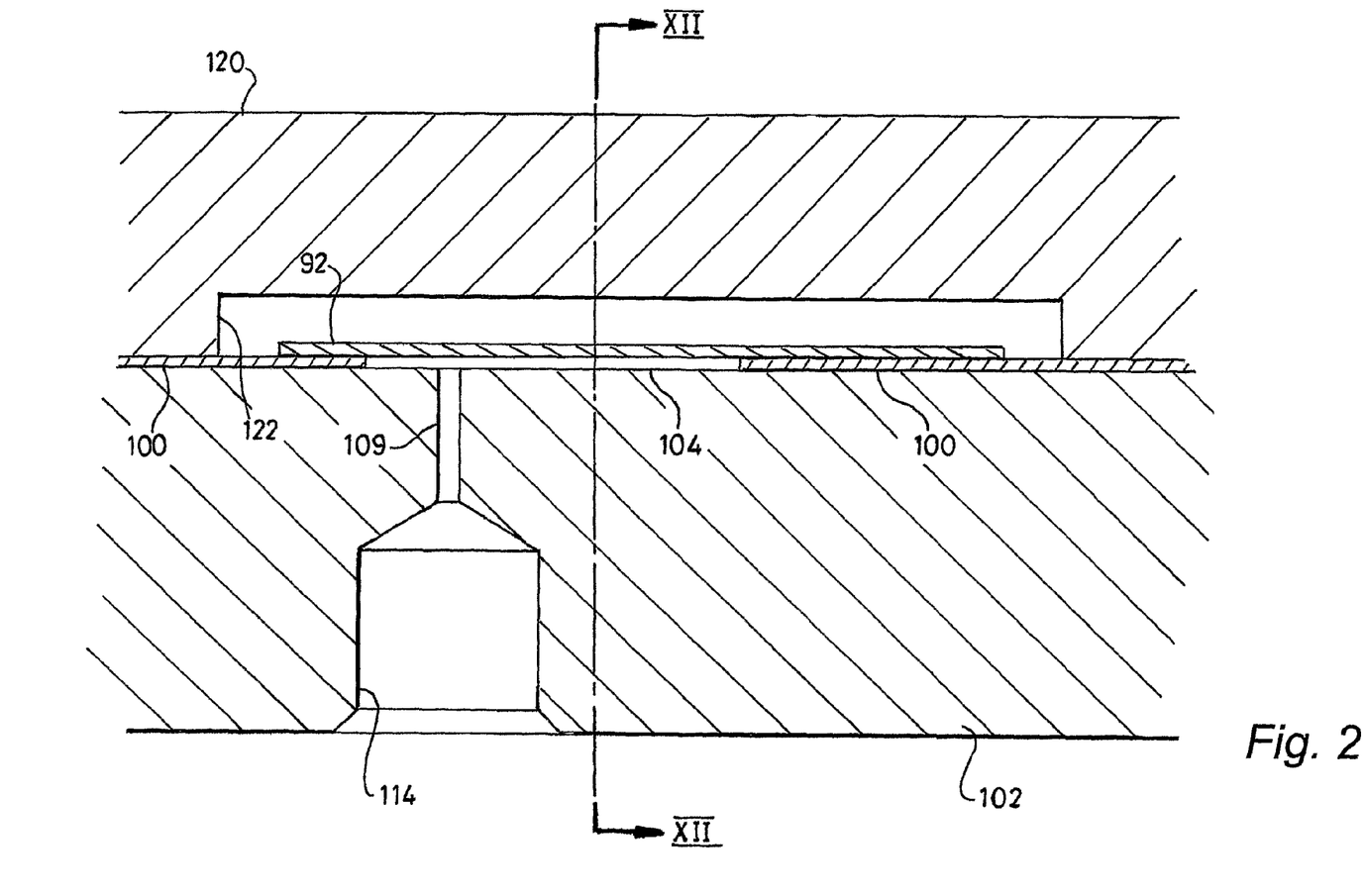
FIG. 2 is a sectional side view of the cartridge.
Figure 3:
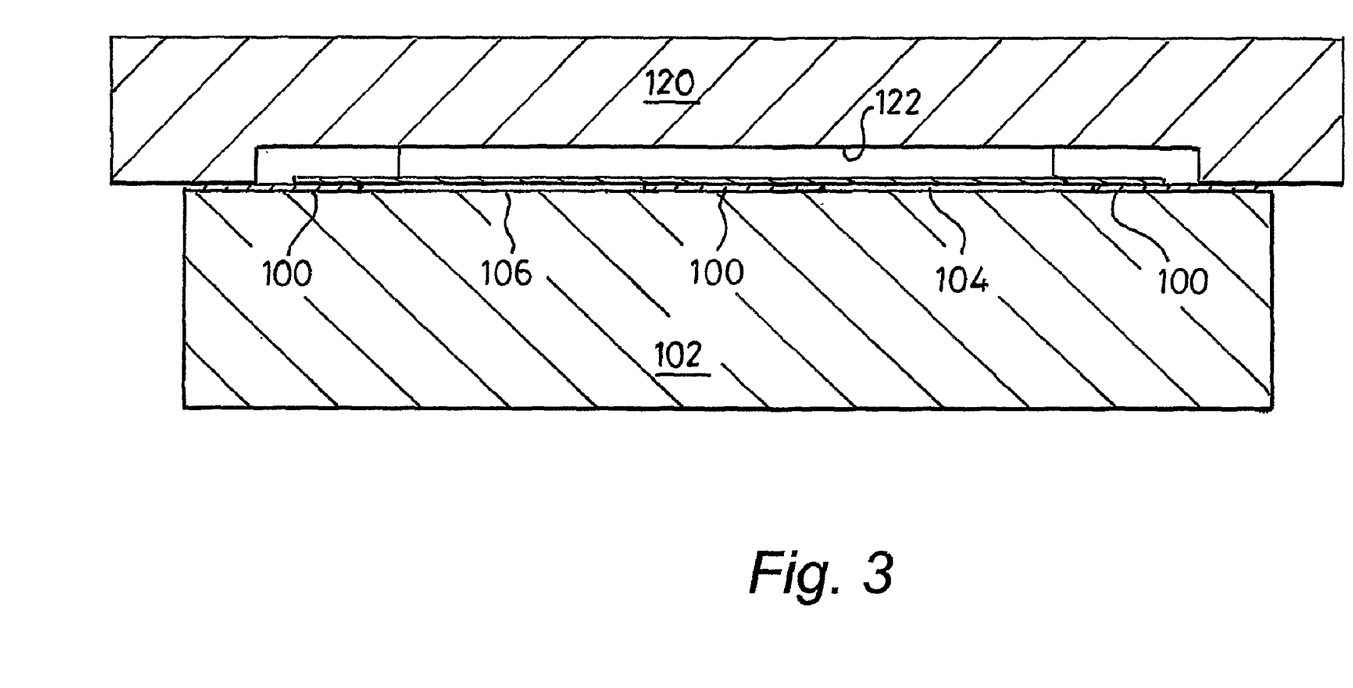
FIG. 3 is a cross-sectional view along the line XII-XII of FIG. 2

In use, the electrical drive applied to the circular electrodes (through the rectangular areas) causes the quartz plate to resonate. This resonance occurs where the electrically driven electrode opposes the ground plate electrode. Conventionally, this causes a transfer shear mechanical mode to be set up under the circular areas of the driven electrodes.

Figure 6:
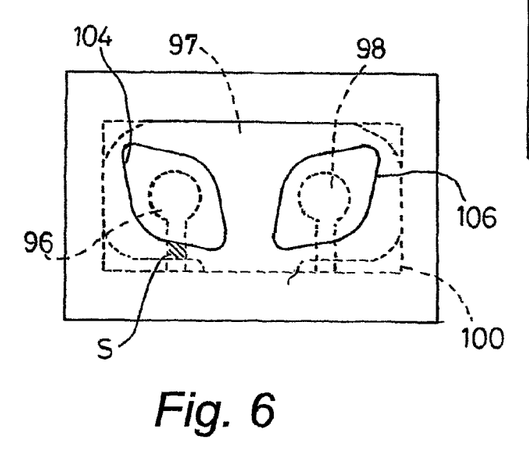
FIG. 6 is a view of the underside of the crystal with an adhesive membrane thereon.

Applicants have discovered, however, that the presence of the drive signal in the rectangular areas can cause the plate under these areas also to oscillate where the ground plain also opposes the rectangular areas. More particularly, with reference to FIG. 6 (which shows the overlay between the adhesive membrane and the electrodes), the region of each rectangular electrode between the edge of the earth electrode 105 and the edge of the flow cell (e.g. the shaded area S in FIG. 6) can give rise to oscillations which can either be reflected off the edge of the crystal 92 or place stresses on the crystal (by virtue of the restraining effect of the adhesive membrane). These effects can vary over time, be hard to predict and therefore are detrimental to the accuracy of the instrument.

Figure 4:
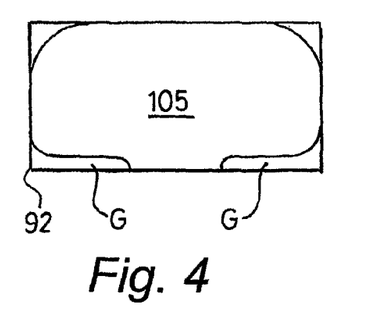
FIG. 4 is a view of the underside of the quartz crystal wafer (and the electrode thereon) used in the cartridge of FIGS. 1-3.
Figure 5:
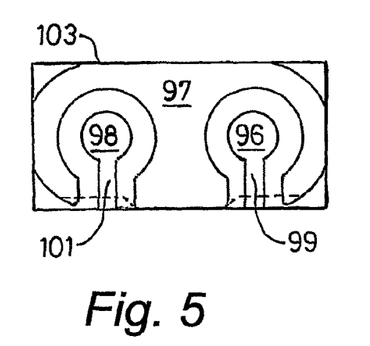
FIG. 5 is a plan view of the crystal (showing the other electrodes)

The effects are at least mitigated by the spacing of the bottom portion of the electrode 105 (as viewed in FIG. 4-6) from the bottom of the crystal 92 so that there is at least an area G at the edge of the crystal where the rectangular portions do not overlap the earth electrode and therefore do not cause the unwanted vibrations.

An improved version of the sensor (forming part of the cartridge) shown in FIGS. 7-9 will now be described.

Figure 7:
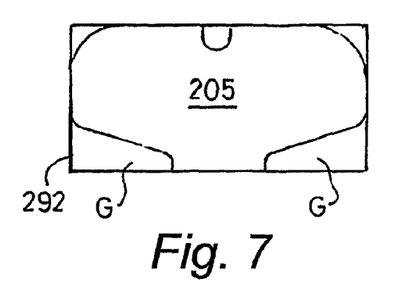
FIGS. 7-9 are views corresponding to FIGS. 4 to 6 respectively, of a modified version of the crystal, membrane and electrodes.
Figure 8:
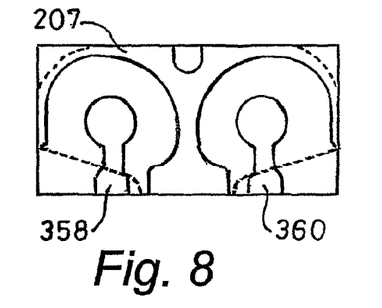
Figure 9:
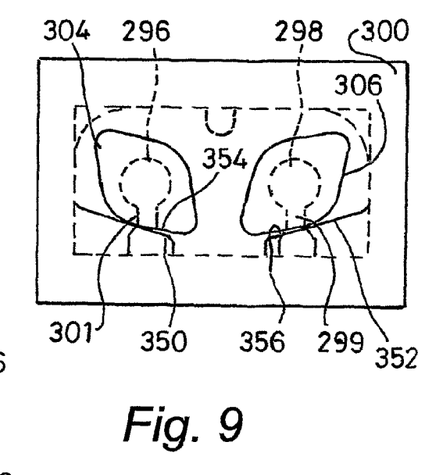

The improved resonator design shown in FIGS. 7-9 has many features in common with or corresponding to those of the design shown in FIGS. 1-3, and these are denoted by the reference numerals used in FIG. 1-3 raised by 200.

In this case, further portions of the earth electrode 205 have been removed where these overlap with the rectangular areas 299 and 301 of the driven electrodes. This change means that there are little or no areas of opposing driven and earth electrodes where the membrane 300 touches the crystal plate 292. Thus the area of crystal under the rectangular portions and in contact with the adhesive membrane does not significantly oscillate when the sensor is driven. As a result, the resistance of plate at resonance is not affected by damping caused by the presence of the membrane contacting this area, and a lower resistance and higher Q factor are achieved.

Figure 10:
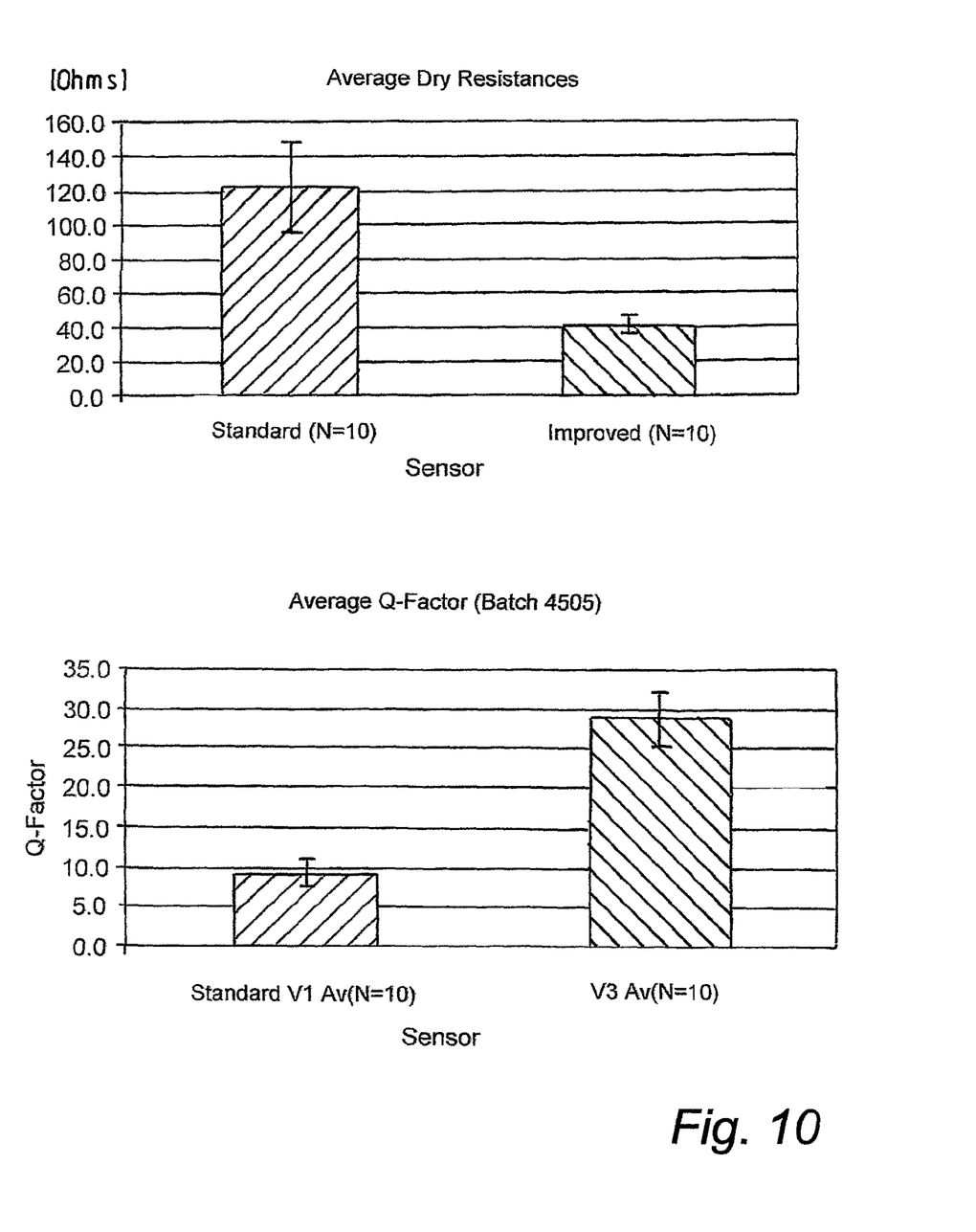
FIG. 10 compares, graphically, the resistance and Q-Factor of the modified version, shown in FIGS. 7 to 9, with the version of sensor shown in FIGS. 1 to 6.

These improvements illustrated in the graph of FIG. 10, in which the left-hand column of each graph shows the resistance or, as the case may be, Q factor of the first embodiment sensor, whilst the right hand column of each graph shows a corresponding measurement for the improved version.

As can be seen from FIG. 9, the lower edges 350 and 352 of the electrode 205, i.e. the edges which extend across the rectangular portions 301 and 299, are inclined in the same sense as the corresponding adjacent edge 354 and 356 of the aperture in the membrane, and hence the flow cell. Thus, the edges of the electrode substantially conform to the adjacent edge of the flow cell, thereby further reducing the overlap mentioned above.

The result of the improvements discussed above is that the sensor, when used in contact with a liquid, has reduced noise and improved unit to unit variance. Additionally, it has been found that the elastic properties of some adhesives may change with time, and that this can give rise to slow changes in the damping of the resonator if substantial portions of the crystal under the membrane are vibrated. This is also undesirable as it leads to baseline drift. With the improved design, the changes in the elastic or mechanical properties of the adhesive or the membrane have a much reduced effect. This can contribute to improved baseline stability and drift which is important in certain types of biochemical assay.

The improvements are optimised when the edge of the membrane does not overlap the edge of the modified electrode boundary at all. However, improvements over the earlier design are also achieved where there is a significant reduction of overlap. It is desirable not to extend a flow cell boundary too far outside the electrode boundary because this exposes uncoated quartz to the analyte fluid. This may result in non-specific absorption of coatings and the like to the quartz which is undesirable.

It can also be seen from FIGS. 8 and 9 that the contacts for the sensor, i.e. the outboard ends 358 and 360 of the rectangular portions, are of an enlarged width. This improves the tolerance of the analytical apparatus to changes in alignment between the Coda pins and the contacts.

The invention claimed is:

1. A cartridge for apparatus for analysing a sample comprising a fluid, the cartridge comprising a flow cell formed from a substantially rigid support surface, a sensor comprising electrical-mechanical transducer for performing said analysis; an adhesive means attaching the sensor to the support surface, and a membrane spacing the sensor from the support to define the flow cell between the support surface and the sensor, the flow cell also having an opening through which, in use, the sample passes.

2. A cartridge according to claim 1, in which, the membrane bounds the flow cell, the opening being provided in the support surface.

3. A cartridge according to claim 1, in which the opening is one of two such openings constituting inlet and outlet ports for the flow cell.

4. A cartridge according to claim 1, in which the adhesive comprises an adhesive layer applied to or formed with the support surface, and a further adhesive layer applied to the sensor so that, in the course of assembly of the cartridge, the adhesive layers on the support surface and the sensor are bought into contact with opposite sides of the membrane to attach the sensor and support surface to the membrane, and hence to each other.

5. A cartridge according to claim 1, in which the membrane and adhesive means comprise a double sided adhesive membrane.

6. A cartridge according to claim 5, in which said double sided adhesive membrane comprises a substrate layer sandwiched between two adhesive layers.

7. A cartridge according to claim 5, in which the membrane comprises a double sided adhesive tape.

8. A cartridge according to claim 7, in which the tape is flexible.

9. A cartridge according to claim 1, in which the membrane is non-compliant to ensure a uniform thickness of the flow cell and a rigid surface to support the transducer when electrical connections to the transducer are applied.

10. A cartridge according to claim 1, in which the membrane comprises a polyester carrier.

11. A cartridge according to claim 4, in which the adhesive layers comprise a cross-linking material which cures to form a non-compliant layer.

12. A cartridge according to claim 11, in which the adhesive layers comprise a pressure sensitive adhesive.

13. A cartridge according to claim 1, in which the support surface comprises a plate, having a fluid connector, constituting the opening, for engaging a complementary connector of a sample delivery system to enable a sample to be supplied to the flow cell.

14. A cartridge according to claim 13, in which the connector is so sized and shaped as to make mating engagement with such a complementary connector.

15. A cartridge according to claim 14, in which the connector is a female connector.

16. A cartridge according to claim 15, in which the female connector comprises a passage for receiving a male connector constituted by a ferrule.

17. A cartridge according to claim 15, in which the connector is one of two such connectors, one for connection to the sample delivery system, the other for connecting an outlet of the flow cell to a sample removal system.

18. A cartridge according to claim 1, in which the electrical-mechanical transducer comprises a plate.

19. A cartridge according to claim 1, in which the sensor includes two electrodes for the connection to circuits for operating the sensor.

20. A cartridge according to claim 19, in which at least one of these electrodes is in registry with the flow cell.

21. A cartridge according to claim 20, in which one of the electrodes is provided on the flow cell side of the side of the connector, the other on the opposite side.

22. A cartridge according to claim 21, in which the electrode on the flow cell side is the earth electrode, the other electrode being the driven electrode.

23. A cartridge according to claim 1, in which the sensor includes thereon contacts for connecting the sensor to circuitry for operating the latter.

24. A cartridge according to claim 1, in which the cartridge includes a cover member attached to the support surface, the sensor being interposed between the support surface and cover member.

25. A cartridge according to claim 24, in which the cover member is so spaced from the sensor as to make no contact with the latter.

26. A cartridge according to claim 24, in which the cover member includes one opening in registry with each sensor for an electrical connector for making contact with the electrode on the non flow cell side of the sensor to connect the sensor to the circuitry for operating the sensor.

27. A cartridge according to claim 1, in which the support surface and the cover member each comprises a respective plate, at least one of which is provided with a bore for use in laterally locating the cartridge.

28. A cartridge according to claim 1, in which the cell is tapered at opposite end regions, the inlet and outlet of the flow cell each being located in a respective one of these regions.

29. A cartridge according to claim 1, in which the flow cell is one of two such cells in the cartridge.

* * * * *